United States Patent [19]
Kragt et al.

[11] 3,989,612
[45] Nov. 2, 1976

[54] ELUTION DEVICE FOR GEL ELECTROPHORESIS

[75] Inventors: Clifford L. Kragt; Harold E. Ballen, both of Kalamazoo, Mich.

[73] Assignee: The Upjohn Company, Kalamazoo, Mich.

[22] Filed: Dec. 26, 1974

[21] Appl. No.: 536,575

[52] U.S. Cl. ............... 204/180 G; 204/299 R
[51] Int. Cl.² ................ G01N 27/26; G01N 27/28
[58] Field of Search ........... 204/180 G, 180 S, 299; 23/230 B

[56] References Cited
UNITED STATES PATENTS

| | | | |
|---|---|---|---|
| 3,255,100 | 6/1966 | Raymond | 204/180 G |
| 3,346,479 | 10/1967 | Natelson | 204/299 X |
| 3,374,166 | 3/1968 | Raymond | 204/299 |
| 3,567,611 | 3/1971 | Michel et al. | 204/180 G |
| 3,719,580 | 3/1973 | Roberts et al. | 204/299 |

*Primary Examiner*—John H. Mack
*Assistant Examiner*—A. C. Prescott
*Attorney, Agent, or Firm*—Woodhams, Blanchard and Flynn

[57] ABSTRACT

A selected fraction is eluted from an electrophoresis separation gel by contacting the opposite sides of a segment of the gel containing the selected fraction with buffer solutions and applying an electrical potential gradient across the gel. The gel segment is held between two elution windows so that the buffer solutions contact a limited area of the gel segment containing the selected fraction whereby only the selected fraction is eluted into one of the buffer solutions.

14 Claims, 7 Drawing Figures

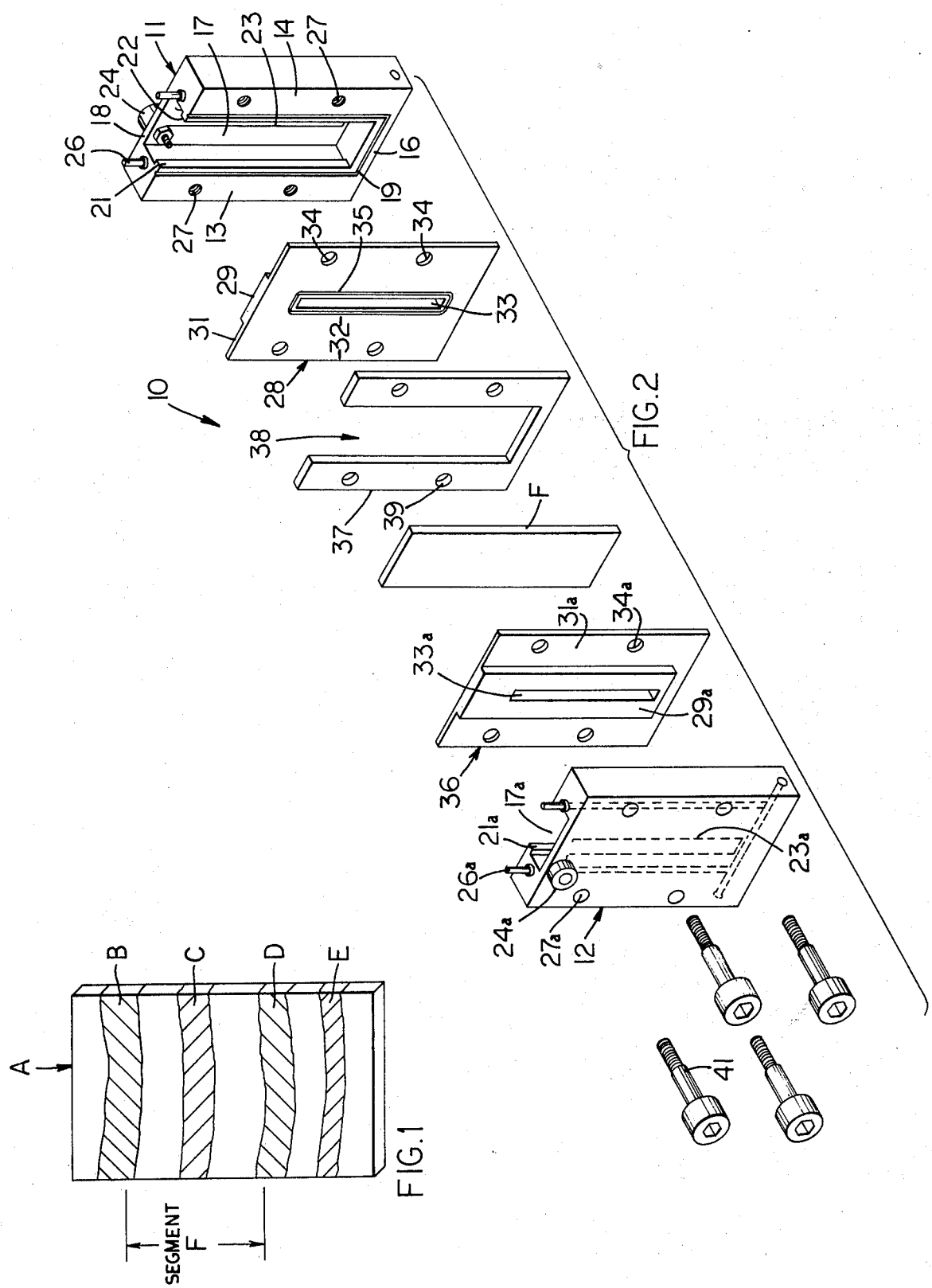

ELUTION DEVICE FOR GEL ELECTROPHORESIS

BACKGROUND OF THE INVENTION

1. Field of the Invention

This invention relates to a method and an apparatus for eluting, by electrophoresis, a selected fraction or fractions present in an electrophoresis carrier or separation gel containing several discrete bands of different fractions.

2. Description of the Prior Art

Excellent fractionations or separations of mixtures of various substances, such as proteins, glycoproteins, nucleotides, nucleic acids, etc., are obtained by electrophoresis using gels as electrophoretic separation matrices. Gels of various materials such as polyacrylamide, starch, agar and gelatin are used for this purpose. Polyacrylamide gels, in the form of elongated cylinders or flat slabs, are particularly preferred for this purpose.

In gel electrophoresis, particles having an effective electrical charge migrate in the gel by the action of an electrical field (potential gradient) applied across the gel. Particles of different charge migrate at different speeds through the gel. Further, referring to particles of equal charge, during their migration through the pores of the three dimensional gel structure, the larger molecules move more slowly than do the smaller molecules because of the molecular sieve effect. Thus the mixture of starting components is fractionated sharply owing to both the differences of the electrical charges of the components of the starting mixture and the differences in their molecular sizes. As a consequence of the electrophoresis, the individual components of the starting mixture are present in the gel as separate, longitudinally spaced, generally transversely extending, distinct bands or zones. These zones can have various widths, measured in the longitudinal direction of the gel, in the range of from about 1 mm to about 1.5 cm. These gel-bound separated fractions can be detected or rendered more readily visible by incubating the gel with fixative-stain solutions. Alternatively, the starting mixture is labelled with a radioisotope and the separated fractions are located by detection of the radioisotope. The gels can be subjected to various analytical determinations in accordance with conventional practices.

It is desired to recover separately individual fractions present as bands in the separation gel, so as to obtain the individual fractions in condition suitable for further analysis. Techniques are known for extraction of a selected gel fraction by cutting the gel cylinder or slab into separate segments, homogenizing each segment (or a plurality of corresponding gel segments from several separation gels) and then eluting same with water or buffer solution and separating the eluate by centrifugation or filtration. The yields of this process are low. In another method of elution, each gel segment (or corresponding gel segments from several separation gels) is homogenized and then is mixed with a new gel solution which is polymerized to form a new gel cylinder or slab. The new gel is subject to electrophoresis until the fraction is swept from the gel by free flow electrophoresis. This process is complex, the yield is poor and extensive dilution of the extracted fraction occurs.

A technique is also known for continuous separation and elution by electrophoresis. This technique is useful as a preparative method wherein milligram quantities of the fractions are recovered. The equipment is complicated and expensive. It is not well adapted for use in the laboratory for effecting microanalytical separations (microgram scale) or ultramicroanalytical separations (nanogram or picogram scale).

Accordingly it is an object of this invention to provide an improved method, and an apparatus for practicing the method, for recovering separately and in a high yield the individual fractions of solutes present in an electrophoresis separation gel.

It is a further object of this invention to provide an improved method, as aforesaid, which is especially adapted for effecting microanalytical and ultramicroanalytical separations, and which provides a high recovery of the desired fraction.

It is a further object of this invention to provide an improved apparatus, as aforesaid, which is relatively simple and inexpensive, which is easy to use and which is reliable and durable.

SUMMARY OF THE INVENTION

According to the invention, there is provided a method and an apparatus for performing the method, in which a selected segment of an electrophoresis separation gel containing one or more bands of fractions or solutes therein is contacted on opposite sides thereof with buffer solutions in a zone extending over only a fractional portion of the total surface area of the gel segment. The zone contains essentially only one band of one solute. A potential gradient is applied between the buffer solutions so that only the solute in the zone migrates by electrophoresis into one of the buffer solutions. Thus, only one fraction or solute is in the latter buffer solution and is available for recovery therefrom. The apparatus is comprised of a pair of chambers for holding the buffer solutions, a pair of elution windows located between the chambers and a means to hold a gel segment securely between the windows. The elution windows have openings of limited width and/or height therethrough so that the buffer solutions can contact only the zone of the gel segment containing a single band of solute. When the electrical potential gradient is applied between the buffer solutions by means of electrodes located in the chambers, only the solute in the zone exposed to the buffer solutions is capable of migrating due to electrophoresis and only that solute will migrate into one of the buffer solutions.

BRIEF DESCRIPTION OF THE DRAWINGS

FIG. 1 is an idealized isometric view of a flat slab type of electrophoresis separation gel containing discrete bands of solutes therein, as indicated by the hatched areas. It is not intended that this figure represent the product of any specific gel electrophoresis separation procedure.

FIG. 2 is an exploded perspective view of the apparatus according to the invention.

DETAILED DESCRIPTION OF THE INVENTION

Referring to FIG. 1, there is shown an idealized illustration of the gel product of a conventional electrophoresis separation procedure. Such procedures themselves are well known and need not be described herein. The gel A is shown as having the shape of a flat slab, but it will be understood that the invention is applicable also to conventional cylindrical electrophoresis separation gels. The gel A is shown as having four discrete bands of solutes B, C, D and E therein. Those bands are spaced longitudinally in the gel A and extend generally transversely thereacross. It will be understood, however, that the bands are shown in FIG. 1 in an idealized state for purposes of clarity in illustration and description. In actual practice, the gel can contain a multitude of bands having various widths in the general range of about 1 mm to about 1.5 cm, and the bands can be inclined with respect to the vertical or somewhat curved. Suffice to say that in electrophoresis separation gels, the components of the starting mixture are separated and are individually present as discrete bands in the gel structure, as is well known.

In order to recover the fraction comprising one of the bands, such as band C in FIG. 1, the gel A is cut transversely into a segment F containing band C, and also containing portions of bands B and D. This segment F is then eluted by the procedure to be described below so as to recover the fraction present in band C in a substantially pure form.

Figure 3:
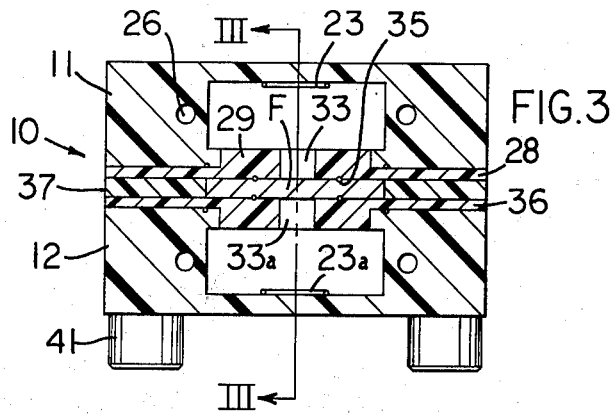
FIG. 3 is a central horizontal sectional view of the apparatus of FIG. 2, in an assembled state.
Figure 4:
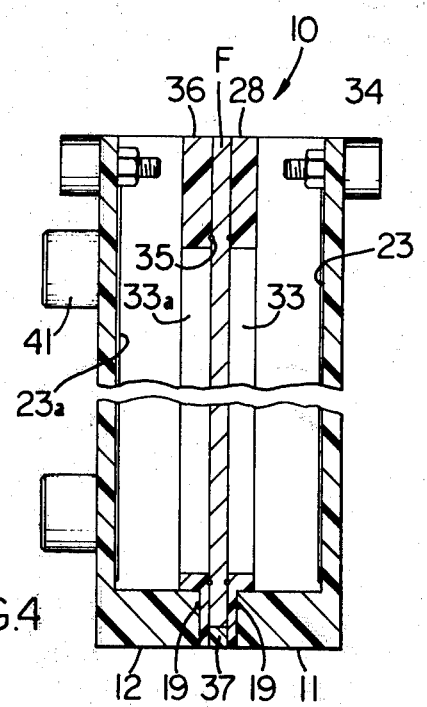
FIG. 4 is a sectional view taken along line III—III of FIG. 3.

Referring to FIGS. 2 to 4, the elution device 10 is comprised of a pair of generally rectangular buffer containers 11 and 12. The container 11 is comprised of side walls 13 and 14 and a bottom wall 16. The walls 13, 14 and 16 define a generally rectangular internal cavity 17 which is open along its axially inner side. The axially inner surfaces of the walls 13, 14 and 16 are flat and coplanar. The outer axial side of cavity 17 is closed by the end wall 18.

A flexible resilient gasket 19 is provided on the coplanar axially inner surfaces of side walls 13 and 14 and of the bottom wall 16. The gasket 19 surrounds the periphery of the cavity 17 on three sides to provide a leakproof engagement with the elution window referred to hereinbelow. The gasket 19 preferably is tubular in cross section, for example, a thin-wall polytetrafluoroethylene tube.

Transverse flanges 21 and 22 are formed on the side walls 13 and 14 adjacent the axially inner surfaces thereof and said flanges project toward each other partway across the open, axially inner side of the cavity 17. These flanges cooperate with the elution window in the manner to be described below.

A generally U-shaped electrode 23, such as a platinum wire, is positioned within the cavity 17 in substantial contact with the end wall 18 for support thereby. One end of the electrode 23 is attached to a connector 24 mounted on the outer side of the end wall 18 for connecting the electrode to one terminal of any conventional source of DC electrophoresis potential. The electrode 23 extends from substantially the top to substantially the bottom of the cavity. The other end of the electrode 23 is embedded in and is supported by the end wall 18.

A coolant passage 26 is provided in the side walls 13 and 14 and bottom wall 16 of the container for removing the ohmic heat generated during electrophoresis. Also, threaded openings 27 are formed in the side walls for receiving the bolts that secure together the parts of the elution device.

The other buffer container 12 is a substantial mirror image of the buffer container 11 and corresponding parts thereof are identified by the same reference numerals with the suffix $a$ applied thereto. The openings 27$a$ in container 12, however, are not threaded.

An elution window 28 is disposed in adjacent sealed contact with the axially inner surface of the buffer container 11. The elution window 28 is comprised of a flat plate having a centrally located boss 29 on the side thereof facing the cavity 17 of the container 11. The boss 29 is rectangular and is sized to fit snugly and extend partway into the cavity 17 to close off the open side thereof. For this purpose the side edges of the boss 29 snugly interfit with the flanges 21 and 22, and the bottom edge of the boss has a similar fit with the bottom edge of the cavity 17. The marginal portions 31 of the elution window surrounding the boss 29 are flat so as to fit in face-to-face engagement with the coplanar flat inner surfaces of the side walls 13 and 14 and the bottom wall 16 of the container 11. The gasket 19 provides a fluid tight seal therebetween. In the embodiment of FIGS. 2 to 4, the opposite surface 32 of the elution window is flat. A passage 33, here a vertically elongated slot, is provided in the elution window 28 to permit flow therethrough. The passage 33 extends completely through the boss 29 so that it opens into the cavity 17 in the central region thereof and the passage is located substantially symmetrically between the legs of the electrode 23. The elution window has openings 34 through which the bolts extend. The elution window has a projecting ridge 35 encircling the passage 33 for penetrating into the gel specimen to improve the sealing effect.

A second elution window 36 cooperates in like fashion with the second buffer container 12. The parts thereof are identified by the same reference numerals with the suffix $a$ added thereto.

The slots 33 and 33$a$ are of essentially the same size and shape and they are aligned with each other. The slots 33 and 33$a$ are sized and shaped so as to overlie and expose only a selected zone of the gel segment F, said zone being a fractional portion of the total surface area of the segment F. This zone covers all or a fraction of the width of the band C.

A flat spacer 37 is provided between the opposing flat surfaces 32 and 32$a$ of the elution windows 28 and 36 for sealing engagement therewith. The spacer has a rectangular cavity 38 of substantially the same size as the cavities 17 and 17$a$, said cavity 38 being of greater vertical extent than the passages 33 and 33$a$. The spacer has openings 39 through which the bolts extend. The segment F of the previously electrophoresed gel material is received snugly into the cavity 38, so that a selected zone thereof is in face-to-face confronting relation to the passages 33 and 33$a$ in the elution windows. The spacer 37 prevents excessive compression of the relatively fragile gel segment F when the device 10 is assembled, so as to maintain the structural integrity of the gel segment. However, the thickness of the gel segment is slightly greater than the thickness of the spacer 37 so that when the parts are secured together, the gel segment is slightly compressed to provide a sealing engagement with the surfaces 32 and 32$a$ of the elution windows. For example the gel segment F can have a thickness of about 2 mm and it can be compressed about 0.1 mm, i.e., to a thickness of about 1.9 mm.

The above described parts are secured together for use by means of bolts 41.

It will be noted that the elution device 10 is open along its upper side. Samples of the buffer solution containing the desired fraction therein can be removed from time-to-time by means of a pipette or similar device. At the end of the elution, the entirety of the buffer solution can be removed in like fashion.

All of the above described parts, except the electrodes 23 and 23a, and the connectors 24 and 24a are made of a suitable electrical insulating material, such as polycarbonate synthetic resin, for example, Lexan synthetic resin, a product of General Electric Company.

Figure 5:
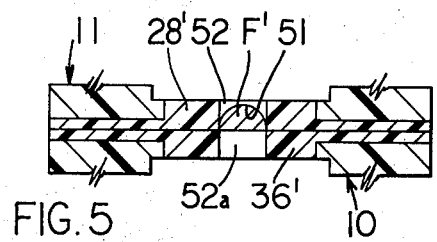
FIG. 5 is a view corresponding to a fragment of FIG. 3 and illustrating a modified construction for use with a gel segment cut from a cylindrical electrophoresis separation gel.
Figure 6:
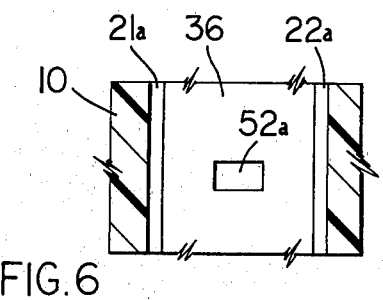
FIG. 6 is a front view of FIG. 5.

FIGS. 5 and 6 illustrate a modified construction in which the gel segment F' is of semicylindrical shape obtained by slicing a cylindrical electrophoresis separation gel lengthwise. The spacer 37 is eliminated and in lieu thereof, one of the elution windows, here the window 28', has a semicylindrical cavity 51 for snugly receiving the gel segment F'. In lieu of the vertical slots 33 and 33a, the elution windows 28' and 36' have horizontal slots 52 and 52a so that only a selected zone along the vertical extent of the gel segment F' is exposed. The slots extend across the entire width of the gel segment.

Figure 7:
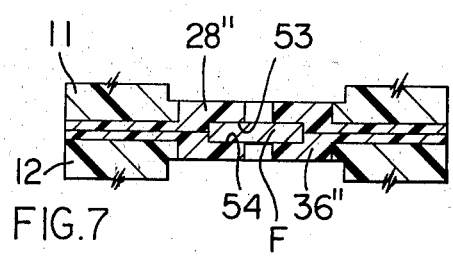
FIG. 7 is a view corresponding to a fragment of FIG. 3 and illustrating another modified construction.

FIG. 7 illustrates a further modification, again showing the spacer 37 eliminated. Here the elution windows 28'' and 36'' have cooperating recesses 53 and 54 in their opposing surfaces to define a cavity for receiving and snugly holding the gel segment F.

Thus, various arrangements can be provided for holding the gel segment and the elution windows can be provided with passages of various sizes, shapes and orientations so as to expose only a selected zone of the gel segment.

OPERATION

The operation has been described generally above, but a further description thereof will be provided to insure a complete understanding of the invention.

The separation gel A will be obtained by a conventional gel electrophoresis procedure. When the gel A has the shape of a flat slab, as illustrated in FIG. 1, the gel is cut to provide the segment F, containing the band C and portions of bands B and D. The gel segment is placed in the holder 37 so that the band C extends substantially vertically in the cavity 38. Then the elution windows 28 and 36, and the buffer solution containers 11 and 12 are assembled thereto and the parts are secured together by the bolts 41. At this time the passages 33 and 33a overlie some or all of the band C, but they do not overlie the other bands in the segment F. Thus only the band C is exposed to the cavities 17 and 17a. The entire assembly is sealed along its sides and bottom by the gasket 19 and also because the marginal portions of the segment F are slightly resiliently compressed between the opposing surfaces 32 and 32a of the elution windows.

Then the cavities are filled with buffer solutions suitable for electrophoresis. Such buffer solutions are well known. The buffer solutions can be selected in accordance with known techniques, taking into account the nature of the fraction to be recovered, the nature of the gel system, the required pH and like factors. The buffers are aqueous solutions which can be acid or alkaline, and they generally have a concentration of about 10% of buffering components. Suitable buffering components include tris (hydroxymethyl)aminomethane, boric acid, glycine, etc., as is well known.

The electrodes 23 and 23a are now connected to an electrophoresis DC power supply unit. Such units are commercially available. They generally supply up to about 400 V and up to about 50 mA. Generally the current intensity is regulated so as to provide a constant current supply. Generally currents higher than 40 mA are avoided to prevent excessive ohmic heating.

The containers 11 and 12 are continuously cooled, during electrophoresis, by circulating coolant through the coolant passages 26 and 26a so that overheating of the gel is avoided. This makes it possible to use higher currents.

The current supply will be continued until most or all of the fraction in contact with the buffer solutions is eluted into the buffer solution in contact with the electrode acting as the positive pole. During this operation some ohmic heat will be generated and this heat is removed by circulating a coolant through the coolant passages 26 and 26a. Generally speaking, cooling is effected so that the temperature of the gel does not exceed about 40° C. If excessive heating occurs, it can be reduced by reducing the current density and lengthening the running time.

Finally, the power supply is terminated and the electrode buffer solutions are decanted. The buffer solution that was in contact with the positive pole contains the desired fraction in substantially pure form. This fraction can be recovered and used for further analysis.

It will be understood that the size and location of the desired fraction to be removed from the separation gel A will have been established in advance by a suitable locating procedure, for example by staining or by radioactive or ultraviolet detection, either on a sample of gel A or on another separation gel prepared under the same conditions. Because of the high reproducibility of electrophoresis gel separations, such will indicate the zone in gel A from which the desired fraction can be recovered. The size and shape of the passages 33 and 33a can thus be determined in advance so as to achieve the desired removal of a single fraction from the gel segment F.

The described apparatus provides the features of ease of loading the gel segment and mechanical stabilization thereof, means to remove the ohmic heat, maintenance of uniform electrical field geometry and maintenance of hydrostatic equilibrium, all of which facilitate the elution operation.

The elution operation is discontinuous and is well adapted for performance in the laboratory. The desired fraction is recovered in a more highly concentrated state than is the case in other elution techniques heretofore used and, thus, the subsequent recovery of the fraction from the buffer solution can be carried out with greater ease and with higher recoveries. The fraction is recovered in a biologically active form i.e., it is not denatured, and it can be analyzed to verify species isolation and activity.

The modification of FIG. 7 can be employed in the same way as described above. In this instance, the gel segment F is supported in the cavity defined by the recesses 53 and 54 in the elution windows.

The modification of FIGS. 5 and 6 employs a semicylindrical gel segment F' obtained by slicing a cylindrical separation gel longitudinally to form the more or less semicylindrical portions, whereas in the embodiment of FIGS. 2–4, the slab was sliced transversely. Hence, in this embodiment the gel segment F' contains all of the bands of fractions formed by the gel electrophoresis separation, and these bands are present as individual longitudinally separate, generally transversely extending bands. Accordingly, the passages 52 and 52a extend transversely and they are of a size and shape to expose only one of the bands or portion thereof. The elution operation itself is the same as previously described.

EXAMPLE

As the starting electrophoresis gel, a slab of polyacrylamide gel is utilized for electrophoresis of an ovine FSH (follicle stimulating hormone) preparation (Papkoff et al., Arch. Biochem, Biophys., 120,434) labelled with I-131, utilizing as buffer tris-boric acid-EDTA of the art at a pH of 8.4, for 3.5 hours, at 15 mA, at a voltage of 150V. A sample of the slab is analyzed by counting the radioactivity of 1 cm sections of the sample to establish the location of the labelled hormone. It is determined that the labelled hormone is present in the gel in a band of approximately 1.0 cm in width. An elution device as illustrated in FIG. 2 is utilized and the width of the passages 33 and 33a is about 1 cm. The slab is cut to obtain a segment having a width of 3 cm, the segment is placed in the holder and the elution device is assembled. A buffer solution of tris-boric acid-EDTA having a pH of 8.4 is placed in chamber 17 and a buffer solution of phosphate buffered saline of the art having a pH of 7.4 is placed in chamber 17a. The electrophoresis power supply is connected so that electrode 23 is negative and electrode 23a is positive. Electrophoresis is carried out at 30 mA at 20 volts for 75 mins. The following results are obtained.

Table 1

| Rate and efficiency of elution | | | | |
| --- | --- | --- | --- | --- |
| Time (min.) | Counts/ min. | Vol. of buffer sample (microliters) | Counts/min. remaining in gel | % elution |
| 0 | 0 | 25 | | 0 |
| 15 | 5746 | 25 | | 15 |
| 30 | 13842 | 25 | | 36 |
| 45 | 25370 | 25 | | 67 |
| 60 | 28728 | 25 | | 75 |
| 75 | 32024 | 25 | | 84 |
| 75 FINAL COLLECTION | 38,400,000 | 30 ml | 7,350,000 | 83 |

The embodiments of the invention in which an exclusive property or privilege is claimed are defined as follows:

1. A method for eluting solutes from electrophoresis separation gels, which comprises:
    placing a preformed, elongated, thin, electrophoresis separation gel specimen containing at least one band of solute therein into a gel specimen holder, said specimen comprising a portion of an electrophoresis separation gel prepared by subjecting a starting mixture of solutes to gel electrophoresis to separate the components of the starting mixture whereby they are present as discrete bands in the gel;
    placing buffer solutions in direct surface contact with the opposite lateral surfaces of an elution area of said specimen which is less than the total surface area of said specimen; and
    applying a DC potential gradient between said buffer solutions and traversing said elution area of said specimen to elute into one of said buffer solutions only the solute in said elution area of said specimen.

2. A method as claimed in claim 1 in which said electrophoresis separation gel specimen is obtained by cutting transversely an elongated flat slab of electrophoresis separation gel having longitudinally spaced bands of solutes therein to obtain a specimen of lesser length than said slab and containing only a portion of said bands, orienting said specimen vertically and placing the buffer solutions in contact only with a vertically extending elution area of said specimen.

3. A method as claimed in claim 1 in which said electrophoresis separation gel specimen is obtained by cutting lengthwise an elongated cylindrical electrophoresis separation gel having longitudinally spaced bands of solutes therein, orienting said specimen vertically and placing the buffer solutions in contact with a horizontally extending elution area of said specimen.

4. An elution device for eluting solute from an electrophoresis separation gel, comprising:
    first and second containers each having a cavity therein for receiving a buffer solution and an electrode disposed in each cavity, means defining a recess for holding an elongated, thin electrophoresis separation gel between said containers and in sealed relationship therewith, and means defining a pair of laterally aligned, through, elution openings extending from opposite lateral sides of said recess to the respective cavities, said elution openings having at least one surface dimension which is shorter than the corresponding surface dimension of said recess so that a zone of limited area of said recess communicates directly through said elution openings with said cavities so that the solute present in the corresponding zone of an electrophoresis separation gel disposed in said cavity can be eluted into one of said buffer solutions by energizing the electrodes to apply a potential gradient transversely across the gel.

5. An elution device for eluting solute from an electrophoresis separation gel, comprising:
    first and second containers having first and second internal cavities for receiving buffer solutions therewithin, said first and second containers having mutually opposed walls with said opposed walls each having elution opening means of limited area extending therethrough from the associated cavity thereof;
    means defining an elongated, thin recess for holding an electrophoresis separation gel specimen containing at least one band of solute therein between said containers and in sealed relationship therewith, both said elution opening means in said opposed walls being of smaller size than said recess and being disposed so that at least portions of both said elution opening means are open to the opposite lateral surfaces of the same zone of limited area of said recess to provide a direct flow path from one cavity to the other cavity transversely through said zone and both said elution opening means, so that the solute in the corresponding zone of an electrophoresis separation gel specimen in said recess is adapted to contact the buffer solutions in the cavities so that the solute can be transferred into one of said solutions; and an electrode disposed in each cavity in association with said elution opening means therein, whereby a potential gradient can be imposed between said electrodes and through said zone for eluting the solute in said zone of the gel specimen transversely into one of said buffer solutions.

6. An elution device as claimed in claim 5 in which said opposed walls are defined by a pair of elution windows disposed between said recess and said cavities, respectively, said elution windows each having an elution slot therethrough and defining said elution opening means, said slot having one dimension smaller than a corresponding one dimension of said recess, said elution slots in said elution windows being in direct axial alignment with each other.

7. An elution device as claimed in claim 5 in which said means defining said recess comprises a U-shaped spacer plate disposed between the opposing surfaces of said walls.

8. An elution device as claimed in claim 6 in which said means defining said recess comprises a spacer element disposed between said elution windows, said spacer element having a gel specimen-receiving recess therein.

9. An elution device as claimed in claim 6 in which each of said containers is comprised of a pair of side walls, a bottom wall and an end wall defining a cavity which is open along the inner side of said container, the associated elution window being engaged in fluid-tight relationship with the inner side of said container and substantially closing the open side of said cavity.

10. An elution device as claimed in claim 9 in which said first and second containers and said elution windows are secured together with the open sides of said cavities facing and being axially aligned with each other and said elution windows are disposed between said open sides with their elution slots in axial alignment with the open sides of said cavities.

11. An elution device as claimed in claim 10 in which each electrode comprises an elongated generally U-shaped electrically conductive member symmetrically disposed with respect to the elution slot in the associated elution window.

12. An elution device as claimed in claim 11 including internal cooling conduit means in said containers for cooling the contents of said cavities.

13. An elution device as claimed in claim 12 wherein said elution windows are plate-like members abutting against the inner sides of said containers, said elution windows having bosses projecting partway into said cavities and closing the open sides thereof, said slots being formed between the edges of said bosses.

14. An elution device as claimed in claim 6 in which said means defining said recess is formed in at least one of the opposing surfaces of said elution windows.

* * * * *